(12) United States Patent
Maurin et al.

(10) Patent No.: US 6,383,994 B1
(45) Date of Patent: May 7, 2002

(54) COMPOSITION FOR WASHING KERATIN MATERIALS, BASED ON DETERGENT SURFACTANT, AN FUNCTIONALIZED SILICONE AND AN ACRYLIC TERPOLYMER

(75) Inventors: Véronique Maurin, Paris; Bernard Beauquey, Clichy, both of (FR)

(73) Assignee: L'Oreal, Paris (FR)

( * ) Notice: Subject to any disclaimer, the term of this patent is extended or adjusted under 35 U.S.C. 154(b) by 11 days.

(21) Appl. No.: 09/671,192

(22) Filed: Sep. 28, 2000

(30) Foreign Application Priority Data

Sep. 29, 1999 (FR) .............................. 99 12170

(51) Int. Cl.⁷ .............................. C11D 3/37; C11D 9/36
(52) U.S. Cl. .................. 510/119; 510/121; 510/122; 510/123; 510/124; 510/125; 510/126; 510/127; 510/128; 510/130; 510/421; 510/422; 510/466; 510/477; 510/398
(58) Field of Search ................................. 510/119, 121, 510/122, 123, 124, 125, 126, 127, 128, 130, 421, 422, 466, 477, 398

(56) References Cited

U.S. PATENT DOCUMENTS 5,573,709 A 11/1996 Wells ..................... 510/122

FOREIGN PATENT DOCUMENTS

| EP | 0 824 914 | | 2/1998 |
|----|-----------|---|--------|
| EP | 824914 | * | 2/1998 |
| EP | 0 825 200 | | 2/1998 |
| FR | 2 779 639 | | 12/1999 |
| WO | 94/06403 | * | 3/1994 |
| WO | 97/35545 | | 10/1997 |

* cited by examiner

*Primary Examiner*—Charles Boyer
(74) *Attorney, Agent, or Firm*—Jacobson Holman, PLLC

(57) ABSTRACT

Composition for washing keratin materials, comprising, in a cosmetically acceptable medium:

i) at least one detergent surfactant;
ii) at least one functionalized silicone; and
iii) at least one acrylic terpolymer consisting of a monomer (a) chosen from a $C_1$–$C_6$ alkyl acrylate and a $C_1$–$C_6$ alkyl methacrylate; of a monomer (b) chosen from a heterocyclic vinyl compound containing at least one nitrogen or sulphur atom, a (meth)acrylamide, a mono- or di ($C_1$–$C_4$) alkylamino ($C_1$–$C_4$) alkyl (meth)acrylate and a mono- or di ($C_1$–$C_4$) alkylamino ($C_1$–$C_4$) alkyl (meth) acrylamide; of a monomer (c) chosen from a urethane produced by reaction between a monoethylenic unsaturated isocyanate and a nonionic surfactant, a copolymerizable ethylenic surfactant monomer, a surfactant monomer of urea type, an allyl ether containing alkylenoxy groups and a nonionic monomer of urethane type.

38 Claims, No Drawings

COMPOSITION FOR WASHING KERATIN MATERIALS, BASED ON DETERGENT SURFACTANT, AN FUNCTIONALIZED SILICONE AND AN ACRYLIC TERPOLYMER

The present invention relates in general to compositions for washing keratin materials, based on a detergent surfactant, a functionalized silicone and an acrylic terpolymer, as well as to a washing process using these compositions.

Functionalized silicones are generally used in shampoo compositions as conditioners to improve the softness, feel and disentangling of the hair. However, it has been found that these silicones lead to the formation of an aesthetically unpleasant layer at the surface of the shampoo. Stabilizers such as crosslinked acrylic polymers of the Carbopol type are frequently used to avoid the appearance of this phenomenon. Nevertheless, these stabilizers have the drawback of reducing the cosmetic performance qualities of shampoos, in particular by making the hair coarser and more charged.

There is thus a need to develop a detergent cosmetic composition, in particular a shampoo, which has a satisfactory aesthetic appearance while at the same time giving acceptable cosmetic performance qualities on keratin materials, i.e. in particular the hair and the scalp.

The Applicant has discovered, surprisingly, that it is possible to formulate compositions for washing keratin materials, in particular shampoos, having the desired properties, by using in these compositions a detergent surfactant and a functionalized silicone combined with a specific acrylic terpolymer, defined below. Specifically, it has been found that the use of the said acrylic terpolymer in the compositions of the present invention gives very good cosmetic properties on keratin materials, in particular the hair, particularly as regards the lightness, softness, smooth feel, suppleness and manageability of the hair.

It has also been found that the compositions of the invention give dried hair which has a generally smoother appearance.

It has also been found that the combinations according to the invention have good skin tolerance.

A subject of the invention is thus compositions for washing keratin materials, essentially characterized in that they comprise, in a cosmetically acceptable medium:

i) at least one detergent surfactant;
ii) at least one functionalized silicone; and
iii) at least one acrylic terpolymer consisting of:
  from 5% to 80% by weight, preferably from 15% to 70% by weight and more preferably from 40% to 70% by weight, of an acrylate monomer (a) chosen from a $C_1$–$C_6$ alkyl acrylate and a $C_1$–$C_6$ alkyl methacrylate;
  from 5% to 80% by weight, preferably from 10% to 70% by weight and more preferably from 20% to 60% by weight, of a monomer (b) chosen from a heterocyclic vinyl compound containing at least one nitrogen or sulphur atom, a (meth)acrylamide, a mono- or di ($C_1$–$C_4$) alkylamino ($C_1$–$C_4$) alkyl (meth) acrylate and a mono- or di($C_1$–$C_4$)alkylamino ($C_1$–$C_4$)alkyl(meth)acrylamide;
  from 0.1% to 30% by weight, preferably from 0.1% to 10% by weight, of a monomer (c) chosen from:
    a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
    a copolymerizable ethylenic unsaturated surfactant monomer obtained by condensing a nonionic surfactant with an $\alpha,\beta$-ethylenic unsaturated carboxylic acid or its anhydride;
    a surfactant monomer chosen from reaction products such as urea of a monoethylenic unsaturated mono- isocyanate with a nonionic surfactant containing an amine function;
    a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200 and preferably less than or equal to 100, m and p denote zero or an integer less than n and $R_2$ is a hydrophobic group of at least 8 carbon atoms and preferably of $C_8$–$C_{30}$;
    and a nonionic monomer such as urethane produced by reaction of a monohydric nonionic surfactant with a monoethylenic unsaturated isocyanate;
  the weight percentages of monomers being based on the total weight of the monomers constituting the terpolymer.

In the washing composition according to the invention, the acrylic terpolymer is present in a proportion of from 0.01% to 20% by weight of active material (A.M.), preferably 0.1% to 10% by weight, relative to the total weight of the composition.

Preferred acrylate monomers (a) in particular comprise $C_2$–$C_6$ alkyl acrylates. Ethyl acrylate is most particularly preferred.

Examples of preferred monomers (b) which may be mentioned are N,N-dimethylaminoethyl methacrylate (DMAEMA), N,N-diethylaminoethyl acrylate, N,N-diethylaminoethyl methacrylate, H-t-butylaminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide. N,N-Dimethylaminoethyl methacrylate is most particularly preferred.

The preferred monomers (c) are the copolymerizable ethylenic unsaturated surfactant monomers obtained by condensing a nonionic surfactant with an $\alpha,\beta$-ethylenic unsaturated carboxylic acid or its anhydride, preferably $C_3$–$C_4$ mono- or dicarboxylic acids or their anhydrides and more particularly acrylic acid, methacrylic acid, crotonic acid, maleic acid, maleic anhydride and most particularly itaconic acid and itaconic anhydride.

The monomers (c) that are particularly preferred correspond to the copolymerizable ethylenic unsaturated surfactant monomers obtained by condensing a nonionic surfactant with itaconic acid. Among the nonionic surfactants which may be mentioned in particular are $C_{10}$–$C_{30}$ fatty alcohols alkoxylated with 2 to 100 mol and preferably from 5 to 50 mol of an alkylene oxide, such as, for example, polyethylene glycol ethers of $C_{10}$–$C_{30}$ fatty alcohols and more particularly the polyethylene glycol ethers of cetyl alcohol which are known as Ceteth in the CTFA dictionary, 7th edition, 1997.

Conventional methods for preparing these acrylic terpolymers are known to those skilled in the art. Such methods include solution polymerization, precipitation polymerization and emulsion polymerization, for example. Terpolymers in accordance with the invention and methods for preparing them are described in particular in patent applications EP-A-0 824 914 and EP-A-0 825 200.

Among these terpolymers, it is preferred in particular to use the <<Structure® Plus>> polymer sold by the company National gtarch, which consists of acrylates, amino(meth) acrylates and $C_{10}$–$C_{30}$ alkyl itaconate, polyoxyethylenated with 20 mol of ethylene oxide, in the form of an aqueous dispersion containing 20% A.M.

In addition to these monomers, the terpolymer can contain other monomers which allow the said terpolymer to be crosslinked. These monomers are used in relatively low proportions, of up to 2% by weight relative to the total weight of the monomers used to prepare the terpolymer. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes. Crosslinking monomers may be, in particular, divinylbenzenes, trivinylbenzenes, 1,2,4-trivinylcyclohexenes, 1,5-hexadienes, 1,5,9-decatrienes, 1,9-decadienes, 1,5-heptadienes, diallyl phthalates, ethylene glycol dimethacrylate, polyethylene glycol dimethacrylate, penta- and tetraacrylates, triallyl pentaerythritols, octaallyl sucroses, cycloparaffins, cycloolefins and N-methylenebisacrylamide.

The functionalized silicones in accordance with the present invention are silicones comprising in their general structure one or more organofunctional groups directly attached to the siloxane chain or attached via a hydrocarbon-based radical. They can be used in native form or in the form of an emulsion or microemulsion.

Mention may be made, for example, of silicones comprising:

a) polyethylenoxy and/or polypropylenoxy groups optionally comprising alkyl groups, such as the product known as dimethicone copolyol sold by the company Dow Corning under the name <<DC 1248>>, by the company Union Carbide under the name <<Silwet>> L 722, L 7500, L 77 or L 711 oil and by the company Rhodia Chimie under the name <<Mirasil DMCO>>, the ($C_{12}$) alkyl methicone copolyol sold by the company Dow Corning under the name <<Q2 5200>>; and the mixture of dimethicone copolyol and of cyclomethicone, such as the product sold under the name <<Q2-3225C>> by the company Dow Corning;

b) (per)fluoro groups, for instance trifluoroalkyl groups, such as, for example, those sold by the company General Electric under the names <<FF.150 Fluorosilicone Fluid>> or by the company Shin Etsu under the names <<X-22-819>>; <<X-22-820>>; X-22-821>>; <<X-22-822or <<FL 100>>;

c) hydroxyacylamino groups, such as those described in European patent application EP-A-0 342 834 and in particular the silicone sold by the company Dow Corning under the name <<Q2-8413>>;

d) thiol groups, for instance in the silicones <<X 2-8360>> from Dow Corning or the products <<GP 72A>> and <<GP 71>> from Genesee;

e) substituted or unsubstituted amine groups, for instance the products sold under the name GP 4 Silicone Fluid and GP 7100 by the company Genesee or the products sold under the names Q2 8220 and DC 929 or 939 by the company Dow Corning. The substituted amine groups are, in particular, $C_1$–$C_4$ aminoalkyl or amino ($C_1$–$C_4$) alkylamino ($C_1$–$C_4$) alkyl groups. The silicones known as amodimethicone and trimethylsilylamodimethicone according to the CTFA nomenclature (1997) are used more particularly;

f) carboxylate groups, for instance the products described in European patent EP 186 507 from Chisso Corporation;

g) hydroxyl groups, for instance the polyorganosiloxanes containing a hydroxyalkyl function, described in patent application FR-A-2 589 476; and in particular polyorganosiloxanes containing a β-hydroxypropyl function;

h) alkoxy groups containing at least 12 carbon atoms, for instance the product <<Silicone Copolymer F 755>> from SWS Silicones and the products <<Abil Wax 2428>>, <<Abil Wax 2434>> and <<Abil Wax 2440>> from the company Goldschmidt;

i) acyloxyalkyl groups containing at least 12 carbon atoms, such as, for example, the polyorganosiloxanes described in patent application FR-A-2 641 185, and in particular polyorganosiloxanes containing a stearoyloxypropyl function;

j) quaternary ammonium groups, for instance in the products <<X2 81 08>> and <<X2 81 09>> and the product <<Abil K 3270>> from the company Goldschmidt;

k) amphoteric or betaine groups, such as in the product sold by the company Goldschmidt under the name <<Abil B 9950>>;

l) by bisulphite groups, such as in the products sold by the company Goldschmidt under the names <<Abil S 201>> and <<Abil S 255>>.

Among these silicones, those comprising substituted or unsubstituted amine groups or quaternary ammonium groups, and dimethicone copolyols, are particularly preferred.

The functionalized silicones can be present in proportions of between 0.01% and 20% by weight relative to the total weight of the composition, and preferably in proportions of between 0.1% and 10% by weight relative to the total weight of the composition.

As mentioned previously, the compositions according to the invention contain at least one detergent surfactant, chosen in particular from anionic, amphoteric, nonionic and cationic surfactanto with detergent properties, and mixtures thereof.

Among the anionic surfactants which may be mentioned are alkaline salts, ammonium salts, amine salts, amino alcohol salts and magnesium salts of the following compounds: alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates.

The alkyl or acyl radical in these various compounds generally consists of a carbon-based chain containing from 8 to 30 carbon atoms.

Among the anionic surfactants which may also be mentioned are fatty acid salts such as oleic, ricinoleic, palmitic and stearic acid salts; coconut oil acid or hydrogenated coconut oil acid; acyl lactylates, in which the acyl radical contains from 8 to 30 carbon atoms.

Surfactants considered as weakly anionic can also be used, such as polyoxyalkylenated carboxylic alkyl or alkylaryl ether acids or salts thereof, polyoxyalkylenated carboxylic alkylamido ether acids or salts thereof, and alkyl D-galactosiduronic acids or salts thereof.

The nonionic surfactants are chosen more particularly from polyethoxylated, polypropoxylated or polyglycerolated fatty acids or alkylphenols or alcohols, with a fatty chain containing 8 to 30 carbon atoms, the number of ethylene oxide or propylene oxide groups being between 2 and 50 and the number of glycerol groups being between 2 and 30.

Mention may also be made of copolymers of ethylene oxide and propylene oxide; condensates of ethylene oxide and of propylene oxide with fatty alcohols; polyethoxylated fatty amides preferably containing 2 to 30 mol of ethylene oxide; polyglycerolated fatty amides preferably comprising 1 to 5 and in particular 1.5 to 4 glycerol groups; polyethoxylated fatty amines preferably containing 2 to 30 mol of ethylene oxide; oxyethylenated fatty acid esters of eorbitan with 2 to 30 mol of ethylene oxide; fatty acid esters of sucrose, fatty acid esters of polyethylene glycol, alkylpolyglycosides, carbamate or amide derivatives of N-alkylglucamines, aldobionamides, amine oxides such as alkylamine oxides or of N-acylamidopropylmorpholine.

The preferred amphoteric surfactants are secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; ($C_8$–$C_{20}$) alkylbetaines, sulphobetaines, ($C_8$–$C_{20}$) alkylamido ($C_1$–$C_6$) alkylbetaines or ($C_8$–$C_{20}$) alkylamido ($C_1$–$C_6$) alkylsulphobetaines.

Among the amine derivatives which may be mentioned are the products sold under the name Miranol, such as those described in patents U.S. Pat. No. 2,528,378 and 2,781,354 and classified in the CTFA dictionary, 7th edition, 1997, under the name Disodium Cocoamphodiacetate, Disodium Lauroamphodiacetate, Disodium Capryloamphodiacetate, Disodium Caproamphodiacetate, Disodium Cocoamphodipropionate, Disodium Lauroamphodipropionate, Disodium Caproamphodipropionate, Disodium Capryloamphodipropionate, Lauroamphodipropionate acid, Cocoamphodipropionate acid.

The cationic surfactants are chosen in particular from salts of optionally polyoxyalkylenated primary, secondary or tertiary fatty amines; quaternary ammonium salts; imidazoline derivatives; or amine oxides of cationic nature.

The preferred quaternary ammonium salts are tetraalkylammonium halides (for example chlorides) such as, for example, dialkyldimethylammonium chlorides and alkyltrimethylammonium chlorides, in which the alkyl radical contains from about 12 to 22 carbon atoms, in particular behenyltrimethylammonium chloride, distearyldimethylammonium chloride, cetyltrimethylammonium chloride, benzyldimethylstearylammonium chloride or stearamidopropyldimethyl(myristyl acetate)ammonium chloride sold under the name <<Cepharyl 70" by the company Van Dyk.

Diacyloxyethyldimethylammonium, diacyloxyethylhydroxyethylmethylammonium, monoacyloxyethyldihydroxyethylmethylammonium triacyloxyethylmethylammonium and monoacyloxyethylhydroxyethyldimethylammonium salts (in particular chlorides or methyl sulphate) and mixtures thereof may be used in particular. The acyl radicals preferably contain 14 to 18 carbon atoms and are obtained more particularly from a plant oil, for instance palm oil or sunflower oil.

The surfactants are used in the compositions in accordance with the invention in proportions that are sufficient to give the composition a detergent nature, generally in a proportion of at least 4% by weight, preferably between 5% and 50% by weight, relative to the total weight of the composition and in particular between 8% and 35%.

The compositions according to the invention have a pH generally of between 3 and 12 and more particularly between 4 and 8.

The cosmetically acceptable medium for the compositions consists of water, of one or more solvents or of a mixture of water and at least one solvent chosen from lower alcohols, alkylene glycols and polyol ethers.

The cosmetic performance qualities of the compositions according to the invention can be improved by adding polyorganosiloxanes other than the functionalized silicones described above, and in particular polyalkylsiloxanes such as linear polydimethylsiloxanes containing trimethylsilyl end groups, such as, for example, and in a non-limiting manner, the <<Silbione>> oils of the series 70047 sold by Rhodia Chimie; the oil <<47 V 500 000>> from Rhodia Chimie, the product <<Viscasil>> from General Electric or <<Mirasil>> from Rhodia Chimie, <<DC 200>> with a viscosity of 0.06 $m^2.s^{-1}$ from Dow Corning or <<AK 300,000>> from Wacker and linear polydimethylsiloxanes containing hydroxydimethylsilyl end groups, such as the oils of the series 48 V from Rhodia Chimie.

The polyorganosiloxanes other than the functionalized silicones are used in the compositions of the invention in proportions that are well known to those skilled in the art.

The cosmetic performance qualities of the compositions of the invention can also be improved by adding a cationic polymer chosen from all those already known per se, in particular those described in patent application EP-A-0 337 354 and in French patent applications FR-A-2 270 846, 2 383 660, 2 598 611, 2 470 596 and 2 519 863.

The cationic polymers used generally have a molecular mass of between 500 and 5 $10^6$ approximately and preferably between $10^3$ and 3 $10^6$ approximately.

Among the cationic polymers which may be mentioned more particularly are quaternized proteins (or protein hydrolysates) and polymers of the polyamine, polyaminoamide and polyquaternary ammonium type. These are known products.

The polymers of the polyamine, polyaminoamide or polyquaternary ammonium type which may be used in accordance with the present invention and which may be mentioned in particular are those described in French patents Nos. 2 505 348 and 2 542 997.

Other cationic polymers which can be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives.

Among the cationic polymers which can be used in the context of the present invention, cellulose ether derivatives comprising quaternary ammonium groups, polysaccharides and in particular cationic guar gum and cyclopolymers of methyldiallylamine or of dimethyldiallylammonium are preferred.

The cationic polymers are used in the compositions of the invention in proportions of between 0.001% and 20% by weight and preferably between 0.05% and 5% by weight, relative to the total weight of the composition.

The compositions according to the invention can furthermore also contain at least one adjuvant chosen from the adjuvants usually used in cosmetics, such as fragrances, preserving agents, sequestering agents, wetting agents, sugars, plant, animal, mineral or synthetic oils, amphoteric polymers, menthol, nicotinate derivatives, agents for preventing hair loss, antidandruff agents, foam stabilizers, propellants, screening agents, dyes, ceramides, vitamins or provitamins, and acidifying or basifying agents or other well-known cosmetic adjuvants.

In one preferred embodiment of the invention, the compositions according to the invention are used as shampoos for washing the hair.

The process for washing keratin materials consists in applying a composition as defined above to wet or dry keratin materials in amounts that are effective to wash them, this application being followed by rinsing after an optional period of leaving the composition to stand on the keratin materials.

The example which follows is intended to illustrate the invention.

SHAMPOO EXAMPLE

| | |
|---|---|
| Propylene glycol | 0.1 g |
| Cocoyl betaine as an aqueous 30% solution | 10 g |
| Hydroxypropyl guar trimethyl ammonium chloride sold by the company Meyhall under the name «Jaguar C13S» | 0.1 g |
| 1- (Hexadecyloxy) -2-octadecanol/cetyl alcohol mixture | 2.5 g |
| Coconut acid monoisopropanolamide | 0.6 g |
| Polydimethylsiloxane containing aminoethyl iminopropyl groups, as a cationic 35% emulsion in water, sold by the company Dow Corning under the name «DC 939», | 7 g |
| Sodium lauryl ether sulphate (2.2 EO) containing approximately 70% A.M. | 22 g |
| Terpolymer of acrylates, amino(meth)acrylates and $C_{10}$–$C_{30}$ alkyl itaconate, polyoxyethylenated with 20 mol of ethylene oxide, in the form of an aqueous dispersion containing 20% A.M., sold by the company National Starch under the name «Structure ® Plus» | 1 g |
| Preserving agents | qs |
| Sterilized demineralized water | qs 100 g |

The pH is adjusted to 5 with citric acid.

After washing with this shampoo, dried hair is found to be soft and supple, to feel and look smooth and to have good manageability.

What is claimed is:

1. A composition for washing keratin materials comprising,
    at least one detergent surfactant,
    at least one functionalized silicone, and
    at least one acrylic terpolymer containing, in amounts based on the total weight of the monomers constituting the terpolymer:
        an acrylate monomer (a) from 5% to 80% by weight selected from the group consisting of a $C_1$–$C_6$ alkyl acrylate and a $C_1$–$C_6$ alkyl methacrylate;
        a monomer (b) from 5% to 80% by weight selected from the group consisting of a heterocyclic vinyl compound containing at least one nitrogen or sulphur atom, a (meth)acrylamide, a mono- or di($C_1$–$C_4$)alkylamino($C_1$–$C_4$)alkyl (meth)acrylate and a mono- or di ($C_1$–$C_4$) alkylamino ($C_1$–$C_4$) alkyl (meth) acrylamide;
        a monomer (c) from 0.1% to 30% by weight selected from the group consisting of:
            i) a urethane produced by reaction between a monoethylenic unsaturated isocyanate and a nonionic surfactant encompassing a block copolymer of 1,2-butylene oxide and of ethylene oxide containing a $C_{1-4}$ alkoxy end;
            ii) a copolymerizable ethylenic unsaturated surfactant monomer obtained by condensing a nonionic surfactant with an α,β-ethylenic unsaturated carboxylic acid or its anhydride;
            iii) a surfactant monomer of urea produced by reacting a monoethylenic unsaturated monoisocyanate with a nonionic surfactant containing an amine function;
            iv) a (meth)allyl ether of formula $CH_2=CR_1CH_2OA_mB_nA_pR_2$ in which $R_1$ denotes a hydrogen atom or a methyl group, A denotes a propylenoxy or butylenoxy group, B denotes ethylenoxy, n is equal to zero or denotes an integer less than or equal to 200, m and p denote zero or an integer less than n and $R_2$ is a hydrophobic group of at least 8 carbon atoms; and
            v) a non-ionic urethane monomer produced by reacting a monohydric nonionic surfactant with a monoethylenic unsaturated isocyanate;
    in a cosmetically acceptable medium.

2. The compogition according to claim 1, wherein the terpolymer is present in a proportion of 0.01% to 20% by weight relative to the total weight of the composition.

3. The composition according to claim 1, wherein the monomer (a) is a $C_2$–$C_6$ alkyl acrylate.

4. The composition according to claim 1, wherein the monomer (b) is selected from the group consisting of N,N-dimethylaminoethyl methacrylate, N,N-diethylaminoethyl acrylate, N,N-diethylaminoethyl methacrylate, N-t-butyl-aminoethyl acrylate, N-t-butylaminoethyl methacrylate, N,N-dimethylaminopropylacrylamide, N,N-dimethylaminopropylmethacrylamide, N,N-diethylaminopropylacrylamide and N,N-diethylaminopropylmethacrylamide.

5. The composition according to claim 1, wherein the monomer (c) is a copolymerizable ethylenic unsaturated surfactant monomer obtained by condensing a nonionic surfactant with itaconic acid.

6. The composition according to claim 1, wherein the acrylic terpolymer consists of acrylates, amino(meth) acrylates and $C_{10}$–$C_{30}$ alkyl itaconate polyoxyethylenated with 20 mol of ethylene oxide.

7. The composition according to claim 1, wherein the acrylic terpolymer further includes a crosslinking monomer.

8. The composition according to claim 1, wherein the functionalized silicone is selected from the group consisting of organomodified polyorganosiloxanes comprising one or more organofunctional groups directly attached to the siloxane chain or attached via a hydrocarbon-based radical.

9. The composition according to claim 1, wherein the functionalized silicone is selected from the group consisting of:
    a) silicones comprising polyethylenoxy or polypropylenoxy groups;
    b) silicones comprising (per)fluoro groups;
    c) silicones comprising hydroxyacylamino groups;
    d) silicones comprising thiol groups;
    e) silicones comprising substituted or unsubstituted amine groups;
    f) silicones comprising carboxylate groups;
    g) silicones comprising hydroxyl groups;
    h) silicones comprising alkoxy groups containing at least 12 carbon atoms;

i) silicones comprising acyloxyalkyl groups containing at least 12 carbon atoms;

j) silicones comprising quaternary ammonium groups;

k) silicones comprising amphoteric or betaine groups; and l) silicones comprising bisulphite groups.

10. The composition according to claim 1, wherein the functionalized silicone comprises substituted or unsubstituted amine groups or quaternary ammonium groups.

11. The composition according to claim 1, wherein the functionalized silicone is present in a proportion of 0.01% to 20% by weight relative to the total weight of the composition.

12. The composition according to claim 1, wherein the detergent surfactant is selected from the group consisting of anionic, amphoteric, nonionic and cationic surfactants, and mixtures thereof.

13. The composition according to claim 12, wherein the anionic surfactants are selected from the group consisting of alkaline salts, magnesium salts, ammonium salts, amine salts and amino alcohol salts of the following compounds:

alkyl sulphates, alkyl ether sulphates, alkylamido ether sulphates, alkylaryl polyether sulphates, monoglyceride sulphates; alkyl sulphonates, alkylamide sulphonates, alkylaryl sulphonates, olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl phosphates, alkyl ether phosphates; acyl sarcosinates, acyl isethionates and N-acyl taurates;

wherein the alkyl or acyl radical comprises a carbon-based chain containing from 8 to 30 carbon atoms;

fatty acid salts of oleic, ricinoleic, palmitic and stearic acid; coconut oil acid or hydrogenated coconut oil acid; acyl lactylates, in which the acyl radical contains from 8 to 30 carbon atoms;

alkyl D-galactosiduronic acids and their salts, polyoxyalkylenated alkyl or alkylaryl ether carboxylic acids or their salts, and polyoxyalkylenated alkylamido ether carboxylic acids or their salts.

14. The composition according to claim 12, wherein the nonionic surfactants are selected from the group consisting of: polyethoxylated, polyoxypropylenated or polyglycerolated fatty acids or alkylphenols or alcohols having a fatty chain containing 8 to 30 carbon atoms, having between 2 and 50 ethylene oxide or propylene oxide groups and having between 2 and 30 glycerol groups; copolymers of ethylene oxide and propylene oxide; condensates of ethylene oxide and of propylene oxide with fatty alcohols; polyethoxylated fatty amides; polyglycerolated fatty amides; polyethoxylated fatty amines; oxyethylenated fatty acid esters of sorbitan; fatty acid esters of sucrose, fatty acid esters of polyethylene glycol; alkylpolyglycosides; carbamate or amide derivatives of N-alkylglucamines, aldobionamides, or amine oxides.

15. The composition according to claim 12, wherein the amphoteric surfactants are selected from the group consisting of: secondary or tertiary aliphatic amine derivatives, in which the aliphatic radical is a linear or branched chain containing 8 to 22 carbon atoms and which contains at least one carboxylate, sulphonate, sulphate, phosphate or phosphonate water-solubilizing anionic group; and $(C_8-C_{20})$ alkylbetaines, sulphobetaines, $(C_8-C_{20})$ alkylamido $(C_1-C_6)$ alkylbetaines or $(C_8-C_{20})$ alkylamido-$(C_1-C_6)$ alkylsulphobetaines.

16. The composition according to claim 12, wherein the cationic surfactants are quaternary ammonium salts.

17. The composition according to claim 1, wherein the detergent surfactant is present in a proportion of at least 4% by weight relative to the total weight of the composition.

18. The composition according to claim 1, wherein the composition has a pH of between 3 and 12.

19. The composition according to claim 1, wherein the cosmetically acceptable medium is water, one or more solvents or of a mixture of water and at least one solvent selected from the group consisting of lower alcohols, alkylene glycols and polyol ethers.

20. The composition according to claim 1, and further comprising at least one linear polydimethylsiloxane containing trimethylsilyl or hydroxydimethylsilyl end groups.

21. The composition according to claim 1, and further comprising at least one cationic polymer.

22. The composition according to claim 21, wherein the cationic polymer is chosen from cellulose ether derivatives comprising quaternary ammonium groups, polysaccharides, and cyclopolymers of methyldiallylamine or of dimethyldiallylammonium.

23. The composition according to claim 22, wherein the cationic polymer is present in a proportion of 0.001 and 20% by weight relative to the total weight of the composition.

24. The composition according to claim 1, and further comprising at least one cosmetically acceptable adjuvant selected from the group consisting of fragrances, preserving agents, sequestering agents, wetting agents, sugars, plant, animal, mineral or synthetic oils, amphoteric polymers, menthol, nicotinate derivatives, agents for preventing hair loss, antidandruff agents, foam stabilizers, propellants, screening agents, dyes, ceramides, vitamins or provitamins and acidifying or basifying agents.

25. A shampoo comprising the composition as defined in claim 1.

26. A method for washing keratin materials, comprising applying at least one composition as defined in claim 1 to the wet or dry keratin materials and rinsing with water.

27. The composition according to claim 1, wherein the acrylate monomer (a) is in an amount of 15% to 70% by weight.

28. The composition according to claim 1, wherein the acrylate monomer (a) is in an amount of 40% to 70% by weight.

29. The composition according to claim 1, wherein the monomer (b) is in an amount of 10% to 70% by weight.

30. The composition according to claim 1, wherein the monomer (b) is in an amount of 20% to 60% by weight.

31. The composition according to claim 1, wherein the monomer (c) is in an amount of 0.1% to 10% by weight.

32. The composition according to claim 1, wherein the functionalized silicone is present in a proportion of 0.1% to 10% by weight relative to the total weight of the composition.

33. The composition according to claim 1, wherein the terpolymer is present in a proportion of 0.1% to 10% by weight relative to the total weight of the composition.

34. The composition according to claim 1, wherein the detergent surfactant is present in a proportion of 5% to 50% by weight relative to the total weight of the composition.

35. The composition according to claim 1, wherein the detergent surfactant is present in a proportion of 8% to 35% by weight relative to the total weight of the composition.

36. The composition according to claim 1, wherein the composition has a pH of between 4 and 8.

37. The composition according to claim 22, wherein the composition contains a cationic polymer in proportions of between 0.05% and 5% by weight relative to the total weight of the composition.

38. The method for washing keratin materials according to claim 26, and further comprising allowing the composition to stand on the keratin materials for a period of time.

* * * * *